(12) United States Patent
Axelgaard

(10) Patent No.: US 8,320,988 B2
(45) Date of Patent: *Nov. 27, 2012

(54) MULTI-ELECTRODE STRUNG ON A COMMON CONNECTOR

(75) Inventor: Jens Axelgaard, Fallbrook, CA (US)

(73) Assignee: Axelgaard Manufacturing Co., Ltd., Fallbrook, CA (US)

( * ) Notice: Subject to any disclaimer, the term of this patent is extended or adjusted under 35 U.S.C. 154(b) by 484 days.

This patent is subject to a terminal disclaimer.

(21) Appl. No.: 12/421,232

(22) Filed: Apr. 9, 2009

(65) Prior Publication Data

US 2010/0261992 A1 Oct. 14, 2010

(51) Int. Cl.
*A61B 5/04* (2006.01)
*A61N 1/00* (2006.01)

(52) U.S. Cl. ........ 600/391; 600/372; 600/393; 607/142; 607/152

(58) Field of Classification Search .................. 600/382, 600/384, 391–393; 607/148–149, 152–153
See application file for complete search history.

(56) References Cited

U.S. PATENT DOCUMENTS

| | | | |
|---|---|---|---|
| 4,122,950 A | 10/1978 | White et al. | |
| 4,736,752 A * | 4/1988 | Munck et al. | 607/152 |
| 4,763,660 A | 8/1988 | Kroll et al. | |
| 5,097,835 A * | 3/1992 | Putz | 600/377 |
| 5,215,089 A | 6/1993 | Baker, Jr. | |
| 6,745,082 B2 * | 6/2004 | Axelgaard | 607/142 |
| 2006/0041301 A1 * | 2/2006 | Ferrari | 607/152 |
| 2009/0209840 A1 * | 8/2009 | Axelgaard | 600/391 |

FOREIGN PATENT DOCUMENTS

WO   WO 2008/157083 A1   12/2008

* cited by examiner

*Primary Examiner* — Linda Dvorak
*Assistant Examiner* — Brian M Antiskay
(74) *Attorney, Agent, or Firm* — Walter A. Hackler

(57) ABSTRACT

A medical electrode includes a moderately conductive flexible member having a top side and a bottom side with a plurality of highly conductive patterns disposed on the conductive flexible member bottom side in a spaced apart relationship. A moderately highly conductive layer disposed on the conductive flexible member bottom side and covering the conductive patterns, for adhering the electrode to a patient's skin. A connector is provided for establishing electrical contact with an external apparatus. The connector includes a leadwire having conductive portions in electrical communication with the conductive patterns and non-conductive portions between the conductive patterns. Control over conductivity between the leadwire conductive portion and the conductive pattern is provided.

5 Claims, 2 Drawing Sheets

MULTI-ELECTRODE STRUNG ON A COMMON CONNECTOR

The present invention generally relates to electrodes and, more particularly, electrodes suitable for transcutaneous nerve and/or muscle stimulation and biological signal recording.

Medical electrodes must provide an even electrical distribution to a patient's skin over an entire surface of the electrode to assure proper coupling. Because of the curvaceous nature of the human body, it is apparent that medical electrodes for use thereon must be flexible not only for confirmation with a patient's skin contours, but also to accommodate relative movement of the patient's skin.

It is well known that inadequate flexing and shaping of the electrode to a patient's contour can result in an irritation of the patient's skin. Electrical "hot spots" due to uneven electrode-skin contact can result in a rash or a burning sensation. A sensation of burning may be felt by a patient within a few minutes after application of the electrical signals during nerve and/or muscle stimulation, while rash conditions generally take a longer period of time to develop.

In order to provide uniform electrical coupling, heretofore developed electrodes have utilized conductive fabrics and foils in combination with a conductive and flexible adhesive in order to uniformly couple electrical signals to and/or from an electrical lead wire, or connector. A number of electrodes have provided impedance compensation for directing electrical pulses from the lead wire uniformly throughout an electrode, such as, for example, U.S. Pat. No. 5,038,796 entitled, ELECTRICAL STIMULATION ELECTRODE WITH IMPEDANCE COMPENSATION, and U.S. Pat. No. 5,904,712 CURRENT CONTROLLING ELECTRODE to Axelgaard. U.S. Pat. No. 4,736,752 teaches the control of current density across an electrode through the use of conductive ink design areas. These patents are incorporated in their entirety herewith by this specific reference thereto.

Many prior art electrodes have compromised the flexibility of the electrode in order to provide adequate current densities over the entire contact area of the electrode. Such electrodes typically have utilized a metallic mesh, or foil, to provide conductivity and utilize a conductive gel between the electrode and the patient's skin in order to accommodate the movement therebetween. Such use of foil or mesh often cause burning or hot spots at electrode edges.

The present invention is directed to a medical electrode having a combination of conductive elements, with selected conductivities which enables assembly of the electrode in a manner hereinbefore not possible. More specifically, the present invention is directed to a medical electrode having a connector disposed on a top surface of a conductive member. This enables automated assembly of the electrode as opposed to conventional manual assembly which in turn reduces unit cost while at the same time providing for controlled and even current density. Interconnection of multiple electrodes may be effected through the use of a leadwire having alternating conductive and non-conductive portions.

SUMMARY OF THE INVENTION

A medical electrode in accordance with the present invention generally includes a moderately conductive flexible member having a top side and a bottom side with a highly conductive pattern, such as, for example conductive ink, printed or transferred to the member bottom side.

A conductive adhesive of moderately high conductivity is disposed on the flexible member bottom side and covering the conductive pattern for adhering the electrode to a patients' skin.

The use of a moderately high conductivity adhesive enables the placement of a connector on the top side of the flexible member while at the same time providing uniform current distribution by the electrode.

In controlling current density, the surface resistivity of the conductive member may be between about $10^2$ and about $10^6$ ohm/cm, the resistivity of the conductive pattern may be between about 0.1 and about $10^2$ ohm and the volume resistivity of the adhesive may be between about $10^2$ and $10^4$ ohm cm. The conductivity of the conductive pattern can be controlled through the use of various grid designs with preselected line widths and spacing as well as thickness and ink compositions.

The connector is disposed over the conductive ink pattern and on the top side of the conductive member, whereas the ink pattern is disposed on the bottom side of the conductive member. This arrangement enables the connectors to be disposed in any selected points within a perimeter of the pattern without affecting current distribution. This flexibility of connector positioning, provided by the present invention, facilitates manufacture of the electrodes. In addition, because the lead wire is not disposed between the conductive pattern and patients' skin, there is no interference with the electrode current distribution as is the case with some prior art electrodes.

Conductivity between the leadwire and the pattern may be controlled by spreading of leadwire strands, using different lengths of leadwire conducting portion, different gauge leadwire strands or partially exposing leadwire strands in the conductive portion.

A non-conductive flexible sheet may be disposed over the connector on the conductive flexible member top side. The non-conductive flexible sheet preferably has dimensions greater than said conductive flexible member causing an overlap thereof. This arrangement facilitates manufacture and also eliminates the need for precise alignment with the conductive flexible member. It also provides a seal of the gel edge and prevents gel from folding around an edge of the conductive flexible member and attaching itself to clothing, etc.

An adhesive is provided for bonding the non-conductive flexible sheet to the top side of said conductive flexible member and also for securing said connector to said conductive flexible member top side.

BRIEF DESCRIPTION OF THE DRAWINGS

The present invention may be better understood with reference to the following detailed description, taken in conjunction with the accompanying drawings, in which.

DETAILED DESCRIPTION

Figure 1:
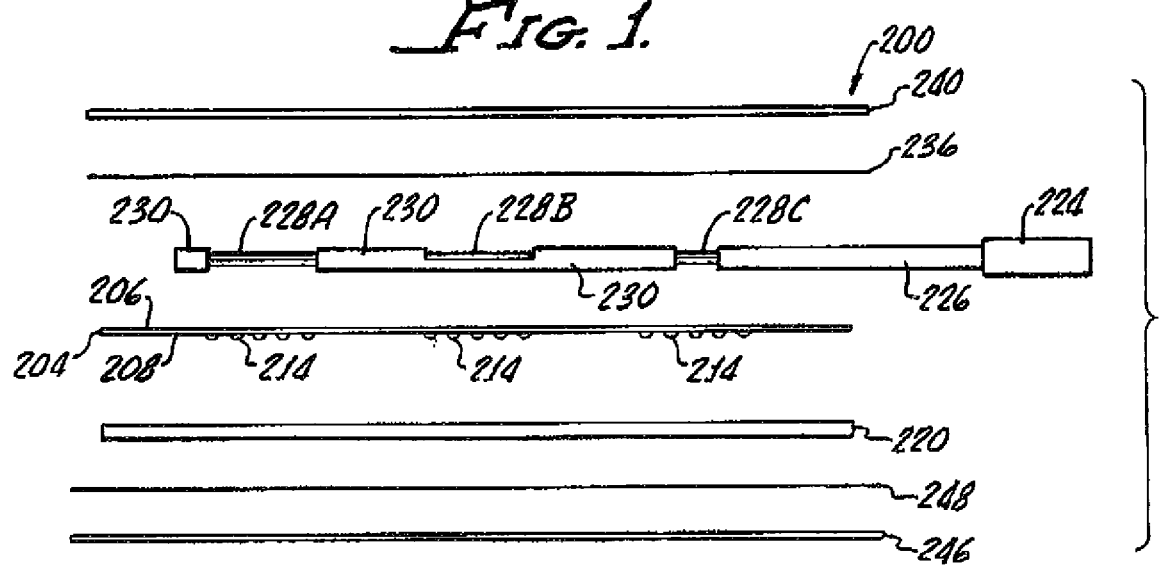
FIG. 1 is an exploded cross-sectional view of a medical electrode in accordance with the present invention generally showing a conductive flexible member, conductive patterns and a connector with a leadwire having conductive portions in electrical communication with the patterns and non-conductive portions between the patterns.
Figure 2:
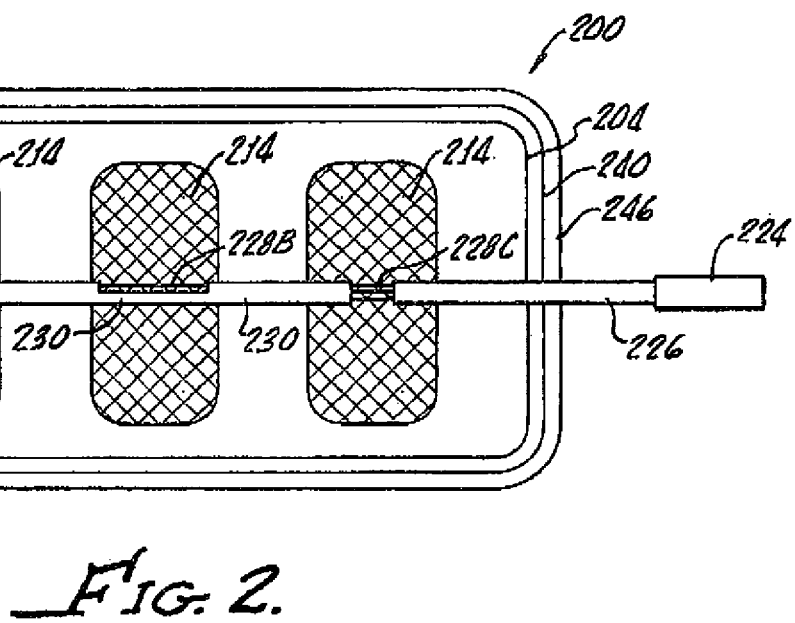
FIG. 2 is a plan view of the electrode shown in FIG. 1.

With reference now FIGS. 1 and 2 there is shown an electrode 200 which includes a moderately conductive flexible member 204, such as, for example, a carbon film, having a top side 206 and a bottom side 208. A plurality of highly conductive patterns 214 are disposed on the bottom side 208 of the conductive flexible member 204. The patterns are disposed in a spaced apart relationship, as shown, and while only three (3) patterns are shown, any suitable number may be used.

As shown, a moderately high conductive adhesive layer 220 is disposed on the conductive flexible member bottom side 208 and covers the conductive patterns 214 while also functioning to adhere the electrode 200 to a patient's skin, not shown. Alternatively, the conductive adhesive layer 220 may be disposed on the conductive flexible member top side 206.

A connector 224 provided for interconnecting the conductive patterns 214 establishes electrical contact with an external apparatus, not shown. The connector 224 includes a leadwire 226 which includes conductive portions 228 for providing electrical communication with the patterns 214 and non-conductive portions 230 between the patterns 214 in order to isolate the patterns from the conductive flexible member 204.

The non-conductive portion, or insulation, 230 on an end of the leadwire 226 is optional. It is only needed if the strands of the leadwire 226 are stiff and protection against cutting through the member 204 and adhesive layer 220 is necessary.

Conductive strand portions 228A, 228B, 228C and non-conductive portions 230 of the leadwire 226 may be prepared by any suitable fashion such as, for example, selective stripping, coating or attaching bands of insulation material.

As best shown in FIG. 2, the conductive strand portions 228A, 228B, and 228C provide several means for controlling conductivity between the leadwire 226 and the conductive patterns 214. As shown the strand 228A may be spread, as illustrated, or with the strands 228B only partially exposed from the insulation, or non-conductive portions 230.

Further, as illustrated with the strands 228C, the non-conductive portion 230 may extend partially over the pattern 214 to control a length of the strands 228C. Also, as shown, one or more of the strands 228C may be of larger or smaller gauge than the remaining strands and may be partially uncovered to provide a means for controlling conductivity between the required conductive portions 228 and on the pattern 214.

A non-conductive flexible sheet, or backing 240, with a non-conductive adhesive layer 236 may be disposed over the leadwire on the conductive flexible member top side 206 with an overlap of the conductive flexible member 204 by a perimeter 240 similar to the embodiments hereinabove described and a removable liner 246 with a release layer 248 is provided to prevent contamination of the electrode 200 prior to use.

Figure 3:
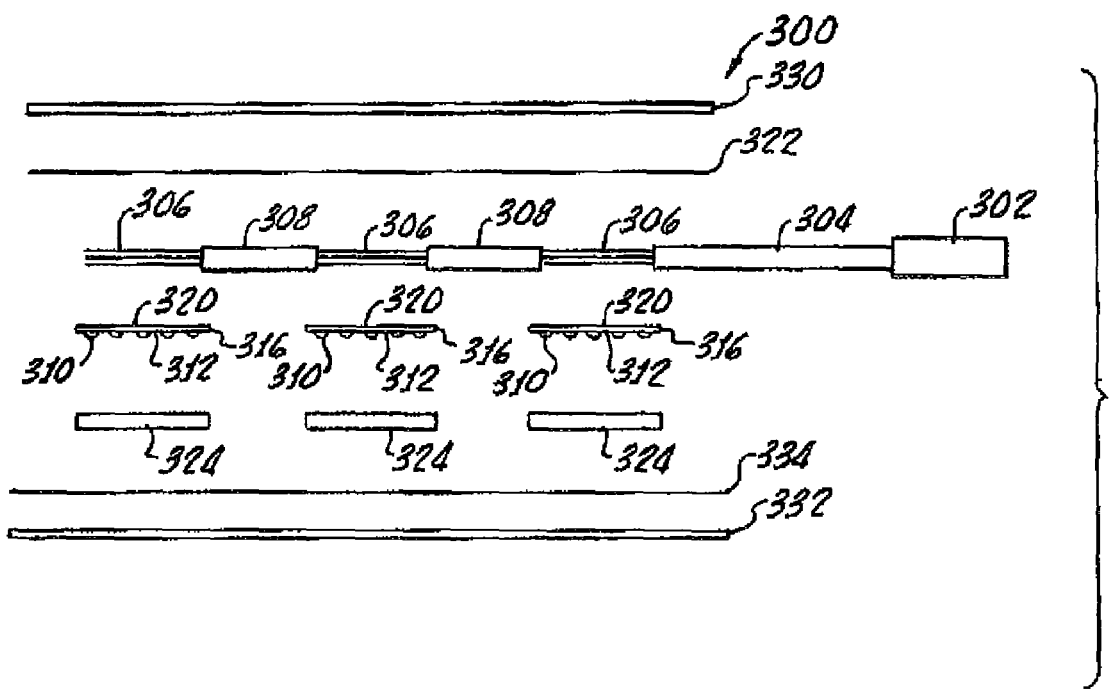
FIG. 3 is an exploded cross-sectional view of an embodiment of the present invention similar to the embodiment shown in FIG. 1 but with separated conductive flexible members, conductive patterns and adhesive layers.
Figure 4:
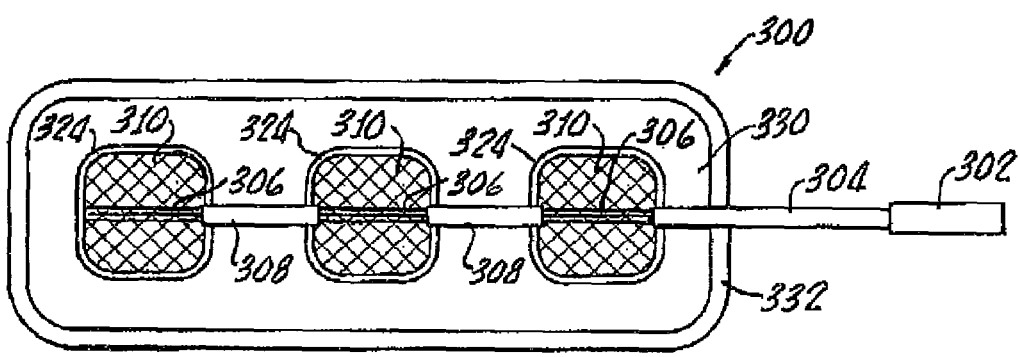
FIG. 4 is a plan view of the electrode shown in FIG. 3.

FIGS. 3 and 4 illustrate an electrode 300 in accordance with the present invention which also uses a conductor 302 having a leadwire 304 having conductive portions 306 and non-conductive portions 308, with the conductive portions 306 in electrical communication with spaced apart highly conductive patterns 310 disposed on bottom sides 312 of a plurality of moderately conductive flexible members 316, the electrical communication occurring through a top side 320 of each of the conductive flexible members 316.

The plurality of conductive patterns are covered by a plurality of moderately high conductive adhesive layers 324 which serve to adhere the electrode 300 and conductive patterns 310 to a patient's skin, not shown.

A non-conductive flexible sheet 330 is disposed over the leadwire 304 on the conductive flexible member top side 320 and the components are bonded by a non-conductive adhesive layer 322. In addition, as hereinabove described a liner 332 with a release layer 334 is provided to prevent contamination of the electrode 300 prior to use.

Although there has been hereinabove described a specific electrode in accordance with the present invention for the purpose of illustrating the manner in which the invention may be used to advantage, it should be appreciated that the invention is not limited thereto. That is, the present invention may suitably comprise, consist of, or consist essentially of the recited elements. Further, the invention illustratively disclosed herein suitably may be practiced in the absence of any element which is not specifically disclosed herein. Accordingly, any and all modifications, variations or equivalent arrangements which may occur to those skilled in the art, should be considered to be within the scope of the present invention as defined in the appended claims.

What is claimed is:

1. A multi-medical electrode system comprising: a moderately conductive flexible member having a top side and a bottom side; a plurality of separate highly conductive patterns disposed on the conductive flexible member in a spaced apart relationship in order to form a string of separate electrodes; a moderately highly conductive adhesive layer disposed on the conductive flexible member for adhering the electrodes to a patient's skin; a connector, including a leadwire disposed on the conductive member and interconnecting the separate electrodes, for establishing electrical contact between the separate electrodes with an external apparatus, said leadwire having conductive portions in electrical communication with the electrodes and non-conductive portions between the electrodes; and leadwire structure for controlling conductivity between the leadwire conductive portions and the electrodes including a length variation of the leadwire conductive portion for each exposed portion along the leadwire.

2. The electrode system according to claim 1 wherein the conductive electrodes are disposed on the conductive flexible member bottom side.

3. The electrode system according to claim 2 wherein the leadwire conductive portions on the flexible member top side are aligned with the conductive patterns disposed on the flexible member bottom side.

4. The electrode system according to claim 1 wherein the conductive pattern is selected from a group consisting of ink, solid metal and conductive plastic.

5. A multi-medical electrode system comprising: a moderately conductive flexible member having a top side and a bottom side; a plurality of separate highly conductive patterns disposed on the conductive flexible member in a spaced apart relationship in order to form a string of separate electrodes; a moderately highly conductive adhesive layer disposed on the conductive flexible member for adhering the electrodes to a patient's skin; a connector, including a leadwire disposed on the conductive member and interconnecting the separate electrodes, for establishing electrical contact between the separate electrodes with an external apparatus, said leadwire having conductive portions in electrical communication with the electrodes and non-conductive portions between the electrodes; and leadwire structure for controlling conductivity between the leadwire conductive portions and the electrodes comprising spacing conductive strands from the leadwire across the separate electrodes.

\* \* \* \* \*